United States Patent
Kline

(10) Patent No.: US 8,061,843 B2
(45) Date of Patent: Nov. 22, 2011

(54) DIAGNOSTIC AND CORRECTIVE APPARATUS AND METHOD

(75) Inventor: Greg Kline, Greentown, PA (US)

(73) Assignee: Paragon Vision Sciences, Inc., Mesa, AZ (US)

(*) Notice: Subject to any disclaimer, the term of this patent is extended or adjusted under 35 U.S.C. 154(b) by 329 days.

(21) Appl. No.: 12/196,483

(22) Filed: Aug. 22, 2008

(65) Prior Publication Data

US 2009/0051875 A1    Feb. 26, 2009

Related U.S. Application Data

(60) Provisional application No. 60/957,598, filed on Aug. 23, 2007.

(51) Int. Cl.
*A61B 3/00*    (2006.01)
(52) U.S. Cl. ........................................ 351/247; 351/219
(58) Field of Classification Search .................. 351/205, 351/206, 211, 212, 219, 233, 241, 246, 247, 351/159, 177
See application file for complete search history.

(56) References Cited

U.S. PATENT DOCUMENTS

| 5,685,420 A | 11/1997 | Martin et al. |
| 6,499,843 B1 | 12/2002 | Cox et al. |
| 2003/0123024 A1* | 7/2003 | Dunn ........................ 351/160 R |
| 2004/0070732 A1* | 4/2004 | Mitsui .......................... 351/247 |

FOREIGN PATENT DOCUMENTS

WO    2008029293    3/2008

OTHER PUBLICATIONS

International Search Report and Written Opinion for International Application No. PCT/US2008/086020 dated Jul. 15, 2009.
Letter from Lancaster Contact Lens, Inc. dated Jan. 5, 2009, addressed to Paragon Vision Sciences.

* cited by examiner

*Primary Examiner* — Ricky Mack
*Assistant Examiner* — Mahidere S Sahle
(74) *Attorney, Agent, or Firm* — Snell & Wilmer L.L.P.

(57) ABSTRACT

This disclosure describes systems and methods which utilize outcomes analysis, empirical and on-eye diagnostic fitting outcomes, and similar patient data to determine and provide a relatively optimal corrective device for the patient, in a single-use and disposable set of devices.

4 Claims, 5 Drawing Sheets

DIAGNOSTIC AND CORRECTIVE APPARATUS AND METHOD

CROSS REFERENCE TO RELATED APPLICATIONS

This application claims priority to U.S. Provisional Application No. 60/957,598 entitled "Diagnostic and Corrective Apparatus and Method," filed Aug. 23, 3007, which is incorporated by reference herein in its entirety.

FIELD OF THE INVENTION

This disclosure generally relates to methods and systems for diagnosing visual acuity deficiencies and providing a relatively optimal corrective device. More particularly, this disclosure relates to providing a single-use set of diagnostic and corrective lenses for a patient.

BACKGROUND

In the treatment of visual acuity deficiencies, correction by means of eyeglasses or contact lenses is used by a large percentage of the population. Such visual acuity deficiencies include hyperopia or far-sightedness, myopia or near-sightedness, astigmatisms (caused by asymmetry of the eye) and presbyopia (caused by loss of accommodation by the crystalline lens).

The selection of the correct contact lens by professionals such as optometrists, ophthalmologists, opticians and/or technicians (referred to herein as a "licensed contact lens fitter") for a patient is important to providing the required level and quality of vision, while simultaneously protecting eye health and delivering appropriate wearing comfort. This relatively "optimal" corrective lens selection is sometimes achieved empirically by determining the most correct lens by utilizing the output from information supplied by instrumentation. In other cases, the "correct" contact lens selection requires patient-specific and/or on-eye diagnosis utilizing a trial lens that has historically been supplied to the licensed contact lens fitter in two fundamental ways.

In the first case, the licensed contact lens fitter provides empirical information to the manufacturer. The manufacturer interprets this supplied data, and provides a trial or diagnostic contact lens to the fitter for on-eye evaluation. Data collected by the licensed contact lens fitter during the patient-specific evaluation process is then supplied to the manufacturer and a different lens is re-supplied to the fitter for the consumer. Sometimes success is achieved with the first lens sent to the fitter by the manufacturer but many times, the "best" lens requires two or more iterations by the manufacturer, and can take weeks or months.

In the second case, and in an effort to speed the diagnostic and dispensing process, the manufacturer will provide the licensed contact lens fitter with a trial or diagnostic set of lenses to be used for all patients. These diagnostic contact lens sets may range in size from 12 to more than 200 lenses, depending on the complexity of the contact lens design and/or the desire of the fitter to improve the probability of having the "correct" lens for the consumer on the premises. The primary intent of trial or diagnostic lens sets is to use the lenses to ascertain or diagnose the "correct" lens for the consumer so that the correct lens can then be ordered from the manufacturer for the consumer. This also means that the diagnostic lenses are used multiple times and with multiple consumers, and disinfected between use. With the larger trial or diagnostic lens sets, it is possible that the "correct" lens may exist within the parameters of the set and, in these cases, some licensed contact lens fitters will dispense or sell the lens from the set. Once this is done, the fitter will then order a replacement trial or diagnostic lens for his set.

In the first case, disadvantages may include the consumer's inconvenience because the licensed contact lens fitter may require the consumer to have multiple visits to the fitting premises to try the various trial lenses ordered from the manufacture. Another drawback may be the time required of the fitter to achieve the correct lens fit. Yet another drawback may be that there is a greater potential for a fitter to accept a marginally good lens for the consumer rather than endure greater inconvenience by ordering a potentially better fitting lens from the manufacturer.

In the second case, drawbacks may include that the trial or diagnostic lens sets can be expensive for the licensed contact lens fitter, thereby inhibiting a large number of fitters from utilizing this method. Another drawback may be that since the lenses are intended to be multi-use, the licensed contact lens fitter must properly disinfect the diagnostic contact lenses in-between use with different consumers to avoid the transmission of disease, or related liabilities. Yet another drawback may include that, despite the fact that larger trial or diagnostic lens sets provide a higher probability of selecting the "correct" lens more effectively and efficiently, the actual procedure of utilizing the set may be confusing.

SUMMARY

Although the methods and systems of the present disclosure may be capable of alleviating some or all of the disadvantages discussed above, it will be appreciated that other disadvantages may be alleviated as well. While the way in which the subject of the present disclosure addresses disadvantages will be discussed in greater detail below, in general, the present disclosure is intended to employ outcomes analysis, optionally utilizing a combination of empirical and patient-specific, on-eye diagnostic fitting outcomes, to deliver an optimal lens for the patient, in a single use and disposable set of lenses. Each set is intended to contain both one or more diagnostic lenses, and one or more corrective lenses for each eye, to be dispensed to the patient. While the number of lenses in the set may vary slightly, in an embodiment, the number of lenses will range from at least 2 and, generally, no more than 6 lenses per eye. In an exemplary embodiment, the number of lenses will be 3 or 4. At least two of the lenses will have at least one different parameter. For example, the lenses may differ in spherical correction and/or cylindrical correction.

Corrective lenses are usually prescribed by an optometrist and/or lens fitter. The fitter may need to prescribe a correction for both eyes, or each eye individually, allowing lenses to be customized for the patient's specific needs. Usually, the amount of correction necessary for both eyes is similar, although in some cases the prescriptions can differ by a substantial margin.

An exemplary process for diagnosing and correcting visual acuity deficiencies includes a contact lens fitter providing specified empirical data collected from an examination of a patient's eyes to the manufacturer. The manufacturer then uses this data to determine the best initial lens that the consumer is predicted to need, based at least in part upon the supplied empirical data, and possibly other data such as third-party historical data. The manufacturer's outcomes analysis may be further based at least in part upon data collected and analyzed from other successfully fitted patients who shared similar initial empirical data. The other lenses in the set will then be determined from an assessment of the manufacturer's outcomes analysis as the most likely relatively "optimal" corrective lenses for that patient.

Furthermore, in various embodiments, the packaging has several compartments that each contain a lens, preferably clearly marked. The markings clearly indicate to the lens fitter which lens should be placed on the eye first, which lens second, then third and so on until the "optimal" corrective lens is determined. For example, markings may be A, B, C, D etc. or 1, 2, 3, 4 etc. or some similar markings that describe the lens selection chronology.

Once the relatively "optimal" lens is selected, the other lenses are designed to be discarded. The optimal lens may then be worn by the patient until additional corrective lenses may be obtained from the manufacturer.

BRIEF DESCRIPTION OF THE DRAWINGS

A more complete understanding of the present invention may be derived by referring to the detailed description when considered in connection with the FIGURES, where like reference numbers refer to similar elements throughout the FIGURES, and.

DETAILED DESCRIPTION

Figure 1:
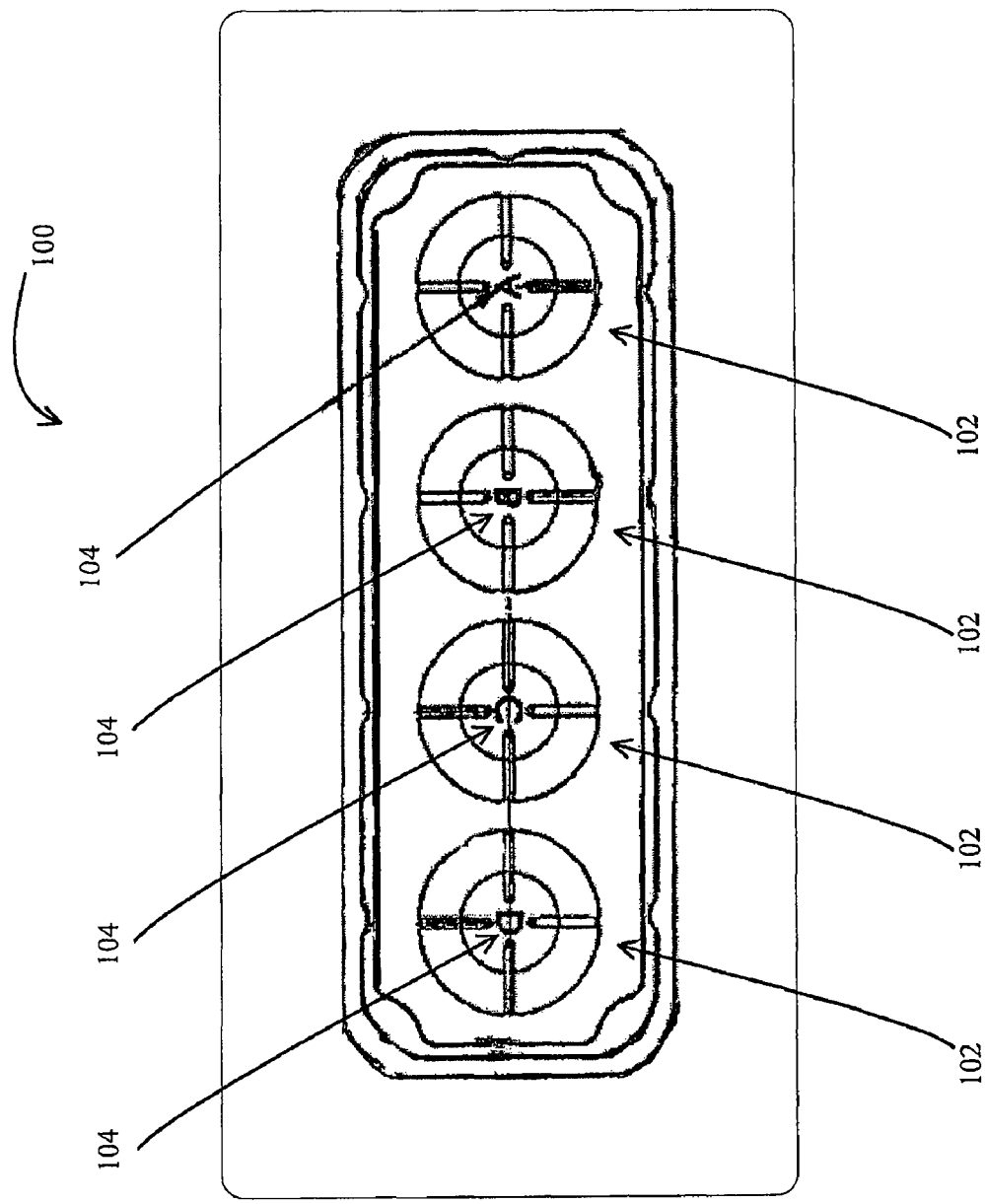
FIG. 1 is an overhead view of a diagnostic and corrective system, according to an embodiment.

The following description is of exemplary embodiments of the invention only, and is not intended to limit the scope, applicability or configuration of the invention in any way. Rather, the following description is intended to provide a convenient illustration for implementing various exemplary embodiments of the invention. As will become apparent, various changes may be made in the function and arrangement of the elements described in these embodiments without departing from the scope and spirit of the invention as set forth in the appended claims. For example, the present invention is described below by referring to various lenses, as well as describing various and specifications of corrective lenses. However, it should be appreciated that such embodiments are non-limiting and that a variety of lenses, data, and/or other elements, fall within the spirit and scope of the present invention.

That said, the present invention generally provides a system and method for providing an optimal corrective lens. In one embodiment, a system of the present invention comprises a set of lenses. While the number of lenses in the set may vary slightly, the number of lenses will range from at least 2 and, generally, no more than 6 lenses. In an exemplary embodiment, the number of lenses will be 3 or 4.

The lenses may have one or more differing parameters so as to create a different effect on a particular user. For example, the differing parameters may cause a user to experience a greater or lesser quality of vision and/or comfort level.

Likewise, the lenses may have differing spherical correction parameters, and/or cylindrical correction parameters. A spherical correction indicates the amount of correction of the refractive error of the eye by adding or subtracting refractive strength symmetrically, by the same amount, along the horizontal and vertical axis.

A cylindrical correction parameter indicates the amount of correction of the refractive error of the eye by adding or subtracting strength along the horizontal axis, the vertical axis, or a diagonal axis. An axis correction may be the horizontal, vertical or diagonal angle of the cylindrical correction. The axis may be measured in a clock face that starts with zero degrees in the 9 o'clock (or east) direction, and increases through 90 and 180 degrees in a counter-clockwise direction. The "spherical" and "cylindrical" specifications may indicate lens strengths in diopters. The "axis" parameter may indicate the direction of the cylinder axis in degrees.

Additionally, the lenses may comprise various prism and base parameters. While not usually used in most prescriptions, they refer to prescription features that are used to treat muscular imbalance or other conditions that cause errors in eye orientation, and are not seen in most prescriptions. A pupillary distance specification, or "PD," is the distance between pupils usually given in millimeters, and written as two values if the prescription is for bifocals or progressive lenses; these are the pupillary distances for the upper and lower lens and differ due to pupillary convergence when looking down.

It will be understood that the lenses of a system of the present invention may differ in any type and number of parameters and fall within the scope of the invention.

In an embodiment, the parameters of the lenses are selected based upon various data, such as empirical data of a patient, patient-specific diagnostic fitting data, and data of third-party optimal fits.

Empirical data of a patient may include the necessary corrections for refraction errors in each eye, individually for distance vision and near vision, which may include four or more correction specifications. Each specification may include a spherical correction in diopters for near/far sightedness and/or presbyopia, a cylindrical correction in diopters combined with the cylinder axis in degrees, correcting for any cylindrical deformation of the eye (i.e., astigmatism). Infrequently, prism and base values may also be specified to correct for a muscular imbalance and/or errors in eye orientation. It will be understood that empirical data may include other desired data relating to the selection of a corrective device.

In an embodiment, the patient-specific data from the patient may include on-eye and/or environmental factors, among other factors and/or data. The patient specific factors may also include whether the patient plays sports, has abnormally dry or wet eyes, etc. The on-eye data may include the patient's visual acuity with the fit and feel of the particular lens, among other data. Patient-specific data may be determined, for example, measuring the eye, vision tests, patient-feedback, etc.

The environmental factors may include the environment where the patient spends a lot of time, such as outdoors, in a dry climate, in a laboratory, in an office in front of a computer screen, and other factors. This data can also be used to determine the lenses to be included in the set.

Data from third-party optimal fits includes any data collected from other successfully fitted patients who shared similar initial empirical data. In an embodiment, the lenses are selected based upon historical data of successful contact lens fits. For example, a database may be compiled that correlates user empirical data (e.g., size, shape and/or curvature of an eye) with optimal contact lens fits. As such, when new empirical data is received, the database may be accessed to determine which contact lenses have historically provided optimal fits for the particular empirical data.

In an embodiment, empirical data is used, alone or in combination with other data, to identify one or more lenses to be included in a system. Each set may contain both the diagnostic lens(es) and one or more corrective lenses from which to determine a relatively optimal lens for each eye to be dispensed to the patient. A diagnostic lens may be any lens suitable for the purpose of viewing the interior of a user's eye, such as during an examination or therapeutic procedure. A corrective lens may be any lens suitable to improve the vision of a user.

In an embodiment, the lenses may be of the same type, in that the lenses may be both diagnostic and corrective-type lenses. This may be desirable as all of the lenses in the system can be used for diagnosis as well as correction. Dual-type lenses may be desirable in the instance where the first lens used is likely to be the relatively optimal lens.

In one embodiment, the system is sent to the fitter and tested upon the patient. The fitter uses the lenses in the system to determine patient-specific data for the patient. It will be appreciated that any other type of data may be used when determining the lenses for inclusion in the set.

For example, FIG. 1 shows an exemplary system 100 for determining and providing a relatively correct lens for a patient in accordance with the present invention. System 100 comprises a set of lenses, including one or more diagnostic lenses and one or more corrective lenses, in receptacles 102. The lenses differ in at least one parameter.

Although four receptacles 102 are shown in FIG. 1, it will be appreciated that any number of receptacles may be included in the system and packaging, without straying from the concepts disclosed herein. Likewise, the number of lenses may vary from patient to patient, fitter to fitter, etc.

As illustrated in the non-limiting example of FIG. 1, indicators 104 may be included to indicate to the lens fitter and/or user which lens to use first, second, third, etc. In this embodiment, indicators 104 may include A, B, C, D, etc. However, other indicators such as 1, 2, 3, 4, etc. and/or other indicators can be used to indicate to the lens fitter the intended lens selection chronology. In an embodiment, indicators may be used to describe one or more characteristics of each lens, such as the curvature, diopters, etc.

In an embodiment, each of the lenses included within the system may differ in at least one parameter, such that each lens may yield different patient-specific data. Moreover, the parameters of the first contact lens in the kit may be used to determine, in whole or in part, the parameters of the other contact lenses included in the kit. This may increase the probability that a relatively optimal lens may be included in the system.

In one embodiment, a method of the present invention comprises the steps of successively inserting each contact lens in the set into an eye of a user, obtaining patient-specific data based thereon, using the patient-specific data to determine whether the contact lens is an optimal fit for the user, and halting the process once an optimally-fitting contact lens has been determined. The method may further comprise the step of discarding all of the contact lenses in the set except the optimal corrective contact lens.

The lens fitter then uses patient-specific information to determine which lens included in the set appears to be a relatively optimal lens to use until other lenses may be ordered. It will be appreciated that at least two of the lenses included in system 100 will have at least one parameter differing from the other, such that a relatively optimal lens, with relatively optimal parameters, may be prescribed or given to the user. Stated otherwise, including at least two lenses having different parameters increases the likelihood that the correct lens will be provided to the user.

Figure 2:
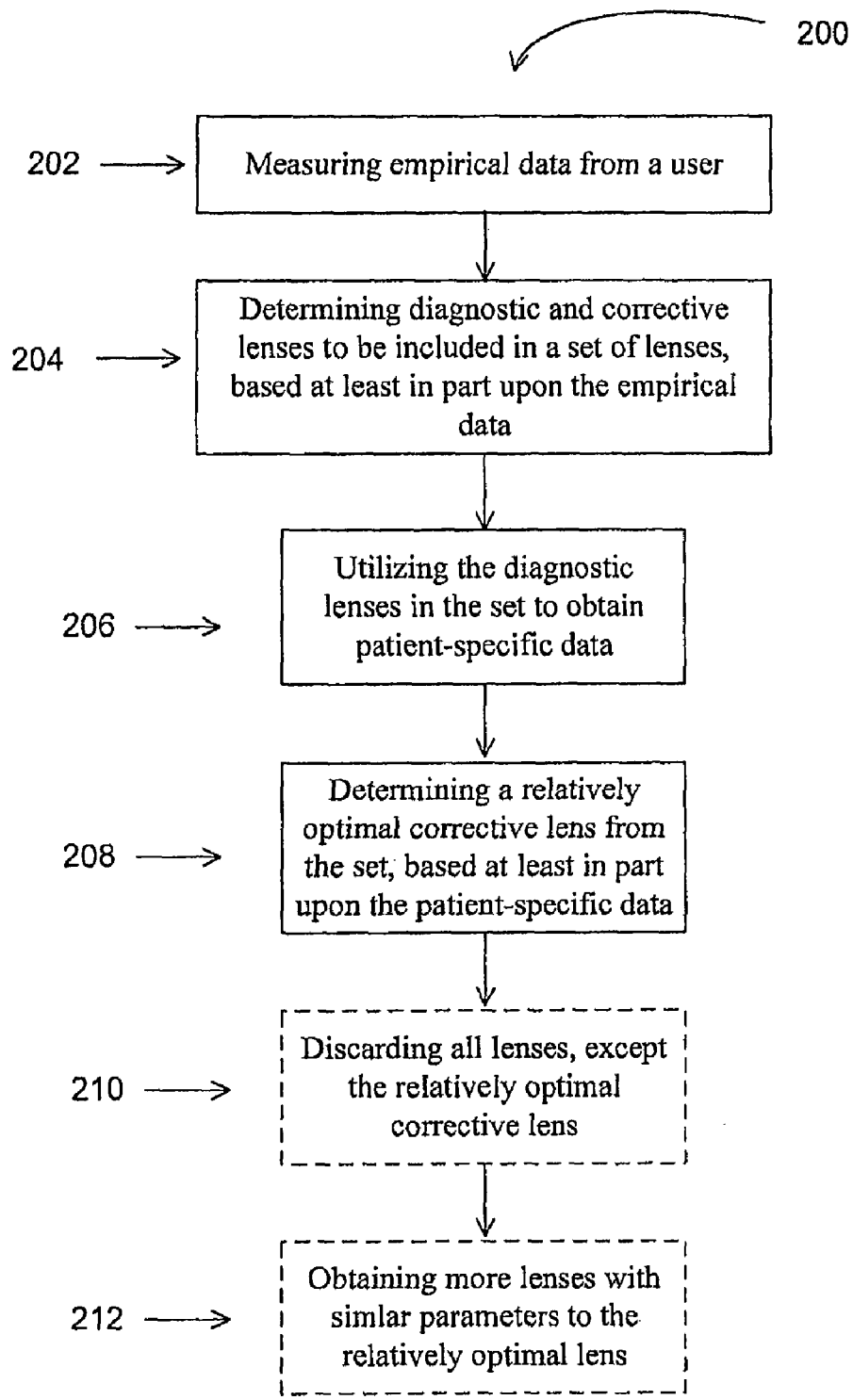
FIG. 2 is a flow diagram of a method for diagnosing and correcting deficiencies, according to an embodiment.

FIG. 2 describes a method 200 for determining and providing a relatively optimal corrective lens for a user. Method 200 includes measuring empirical data from a user 202, determining diagnostic and corrective lenses to be included from a set of lenses, based at least in part upon the empirical data 204, using the diagnostic lenses in the set to obtain patient specific data 206, determining a relatively optimal corrective lens from the set, based at least in part upon the patient-specific data 208. Method 200 may further include the steps of discarding all lenses 210 except the relatively optimal corrective lens, and obtaining more lenses 212 with similar parameters to the relatively optimal lens.

Measuring empirical data from the user 202 may include an eye test at an optician or other lens fitter. The data from that eye test may include empirical data 204, which can be used to determine diagnostic and corrective lenses to be included in the set of lenses.

The diagnostic and corrective lenses included in the set are then sent to the lens fitter. The lens fitter then starts with the first identified lens in the set to obtain patient-specific data about the fit and feel of the lens. This data is used to determine a relatively optimal corrective lens from the set 208.

Once the relatively optimal lens is identified for the user, the user keeps that lens and discards other lenses 210. In this manner, the time needed to determine the relatively optimal corrective lens for the patient is reduced. Additionally, since all other lenses in the set are to be thrown away, this can improve the hygiene of the lenses used for correction and/or diagnostics. Another added benefit may be the cost savings to the lens fitter by reduction of the number of lenses stocked. Further advantages of this method may include higher probability of selecting the relatively optimal corrective lens more effectively and efficiently for the user.

Once the relatively optimal lens is determined, the patient uses the relatively optimal lens 212 and orders or obtains more replacement lenses with the same or similar parameters to the relatively optimal lens.

In an embodiment, a fitter may insert a lens from the system into an eye of a patient, observe and collect patient-specific data from each of the lenses, and then use the patient-specific data to select a relatively optimal corrective device for the patient. Once a relatively optimal corrective lens has been determined, the other lenses of the kit may be discarded.

The relatively optimal lens may then be used by the patient, the other lenses in the system discarded, and more lenses with the same or similar parameters to those of the relatively optimal lens may then be ordered.

Figure 3:
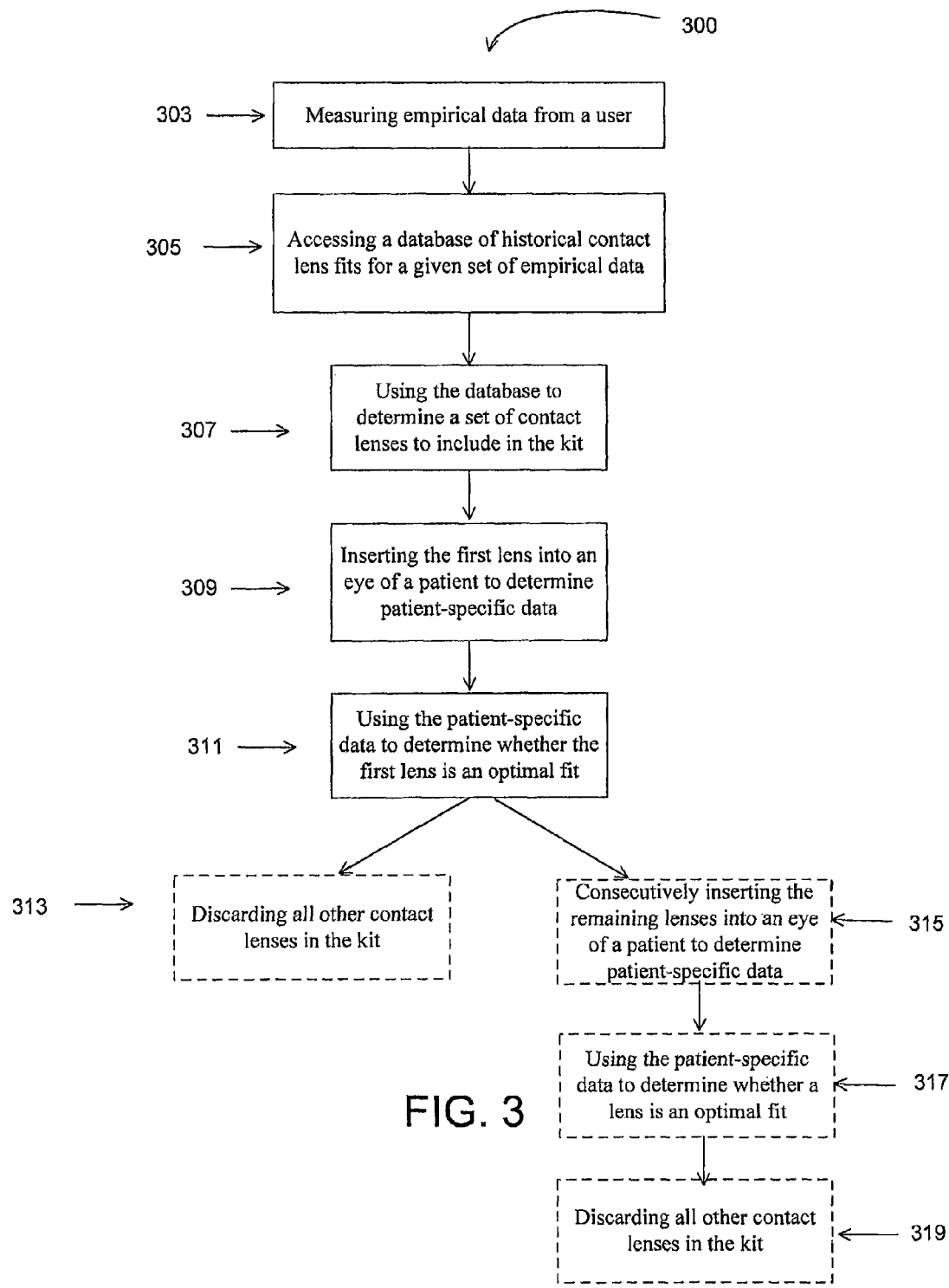
FIG. 3 is a flow diagram of an embodiment of a method of the present invention.

As shown in FIG. 3, another exemplary method 300 includes the steps measuring empirical data of a user 303, accessing a database of historical contact lens fits for a given set of empirical data 305, using the database to determine a set of contact lenses $X_a, X_b \ldots X_n$ to be included in a kit 307, inserting lens $X_a$ into an eye of a patient to determine patient-specific data 309, using the patient-specific data to determine whether $X_a$ is an optimal fit 311.

If $X_a$ is an optimal fit, the method may further include the step of discarding all other contact lenses in the kit 313. If $X_a$ is not an optimal fit, the method includes the step of consecutively inserting lenses $X_b \ldots X_n$ into an eye of a patient to determine patient-specific data 315 and using the patient-specific data to determine whether the lens is an optimal fit lens 317. Once an optimal contact lens has been determined, all other contact lenses in the kit may be discarded 319.

Figure 4:
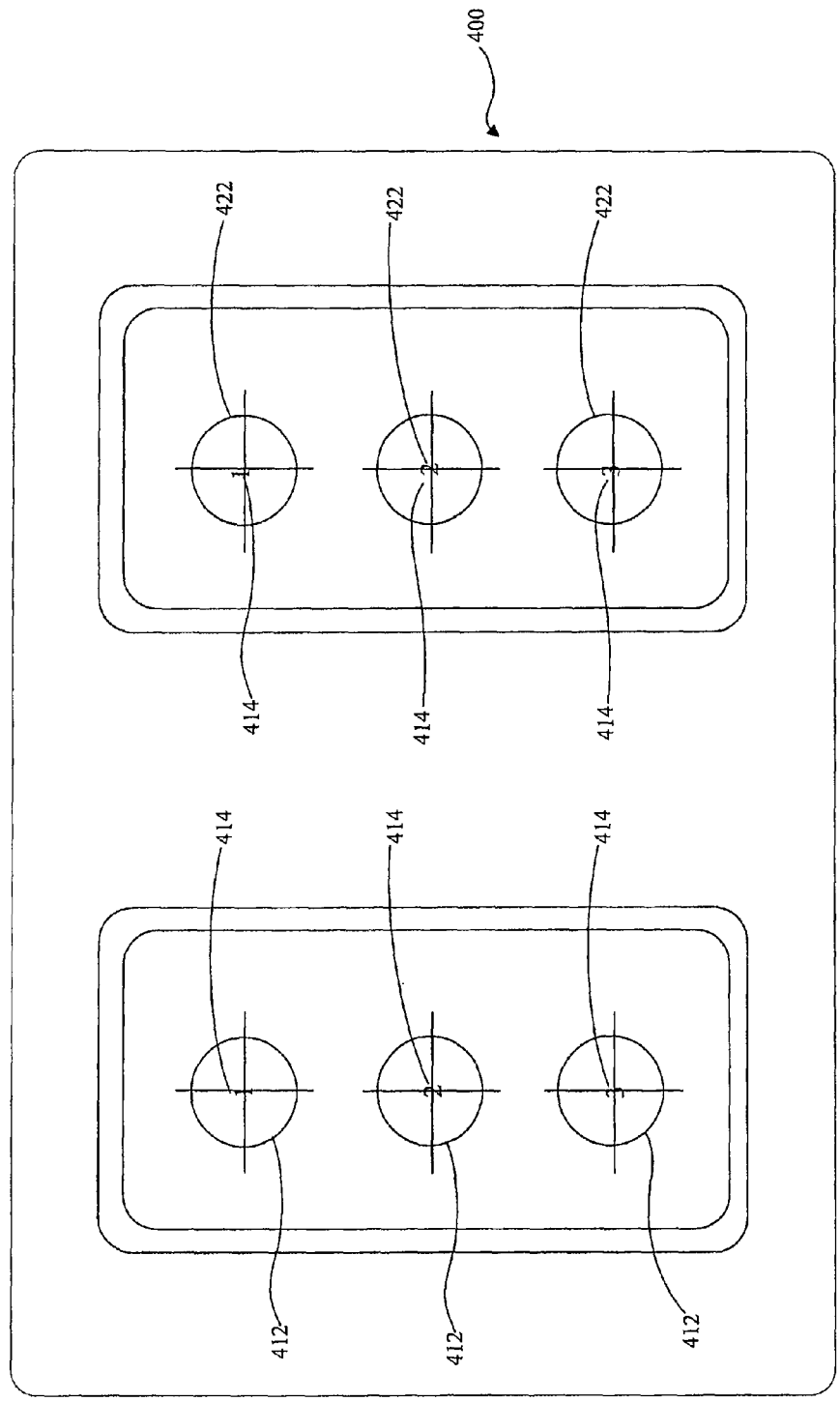
FIG. 4 is an overhead view of an embodiment of a kit of the present invention.

In another embodiment, an exemplary system of the present invention allows a user to try more than one contact lens design within the same patient visit. For example, as illustrated in FIG. 4, system 400 comprises a first set of lenses 412 having a first design, and a second set of lenses 422 having a second design. The lenses comprising the first set 412 and/or the lenses comprising the second set 420 may differ in one or more parameters, such that each lens has a different effect and thus yields different patient-specific data. The system may include indicators 414 to indicate to the fitter which lens to use first, second, etc.

As shown in FIG. 4, a system may comprise two sets of lenses having differing designs. However, it will be understood by skilled in the art that a system of the present invention may comprise any desired number of sets of lenses of different designs, and varying number of lenses within the sets, and fall within the scope of the present invention. Moreover, a system may contain one or more diagnostic lenses and one or more corrective lenses.

Figure 5:
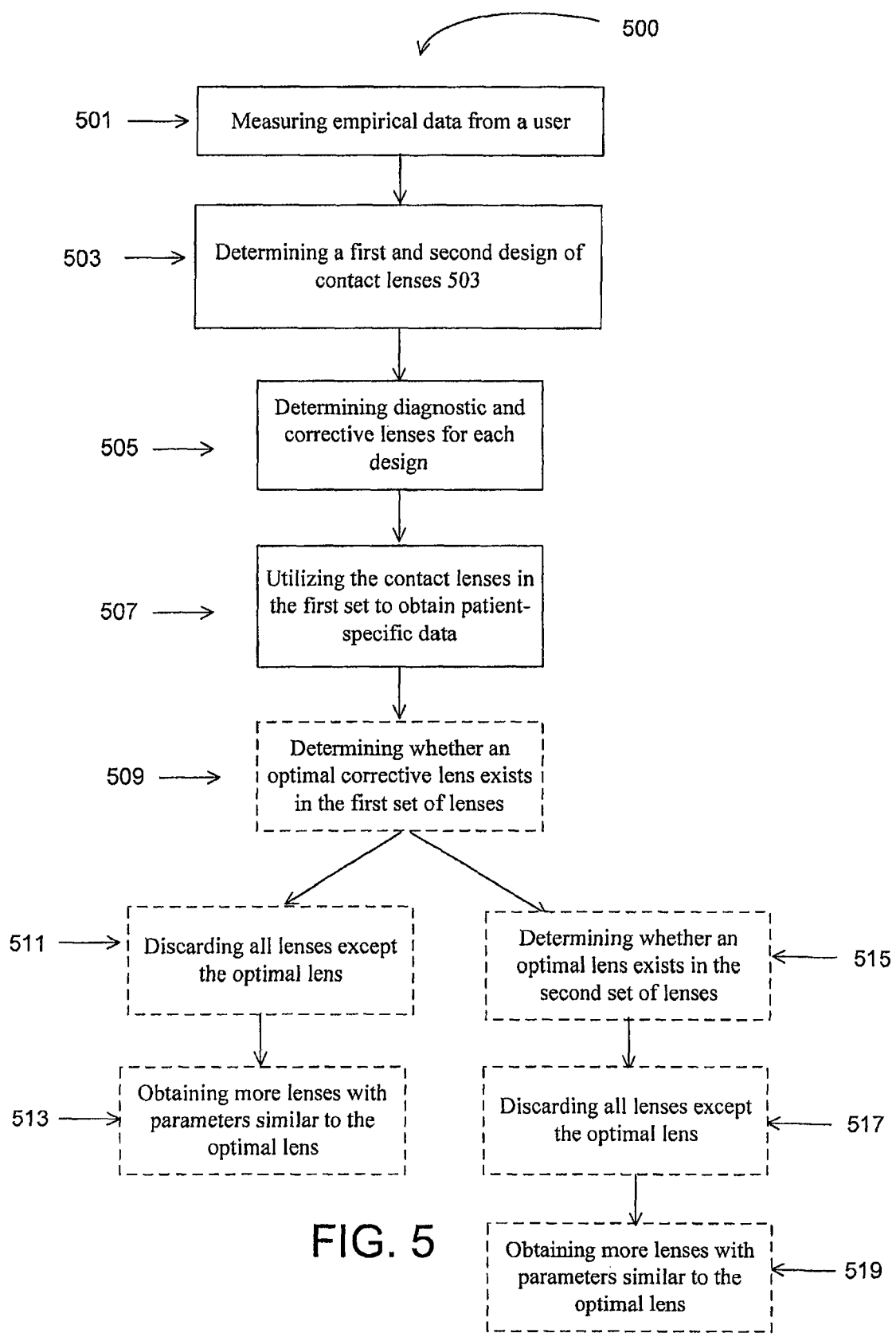
FIG. 5 is a flow diagram of an embodiment of a method of the present invention.

FIG. 5 describes a method 500 for determining and providing an optimal corrective lens for a user. Method 500 may include the steps of measuring empirical data from a user 501, determining a first and second design of contact lenses 503, determining diagnostic and corrective lenses for each design to be included as a first and second set of contact lenses 505, utilizing the contact lenses in the first set to obtain patient specific data 507, and determining whether an optimal corrective lens exists in the first set of lenses 509.

If an optimal corrective lens exists in the first set of lenses, method 500 further includes the steps of discarding all lenses except the optimal corrective lens 511, and obtaining more lenses with similar parameters to the optimal lens 513.

If an optimal lens does not exist in the first set of lenses, method 500 further includes the steps of determining whether an optimal corrective lens exists in the second set of lenses 515. If the optimal corrective lens exists in the second set of lenses, discarding all lenses except the optimal corrective lens 517, and obtaining more lenses with parameters similar to the optimal lens 519.

In an embodiment, based at least in part upon the patient-specific data and other data, a relatively optimal corrective lens may be identified from the corrective lenses included in the set. This lens may then be used by the patient, and more corrective lenses with the same specifications as the relatively optimal lens, may be ordered from the manufacturer. The diagnostic and corrective lenses in the set may be all of the same type, in that they may all be capable of yielding on-eye data, and can be used as corrective lenses.

This may reduce the time needed to determine the relatively optimal corrective lens for the patient. Additionally, since all other lenses in the set are to be thrown away, this may improve the hygiene of lenses used for corrections and/or diagnostics. Another added benefit may be a cost savings to the fitter by not having to stock a multitude of lenses. Further advantages may include higher probability of selecting the relatively optimal corrective lens more effectively and efficiently.

It will be appreciated that although embodiments disclosed are directed toward diagnosing and correcting visual acuity deficiencies, and in particular to contact lenses, the methods and systems disclosed herein can be used for other diagnosis and correction, such as orthodics, orthodontics, and/or many others. Furthermore, this disclosure should not be limited by the systems and materials used.

Finally, it should be understood that various principles of the invention have been described in illustrative embodiments only, and that many combinations and modifications of the above-described structures, arrangements, proportions, elements, materials and components, used in the practice of the invention, in addition to those not specifically described, may be varied and particularly adapted to specific patients and their requirements without departing from those principles.

I claim:

1. A system for determining an optimal contact lens, said system comprising:
a plurality of diagnostic contact lenses to be successively placed on a single eye, each of said plurality of contact lenses differing in at least one parameter such that each of said plurality of contact lenses is operable to provide different patient-specific data when inserted in an eye of a user, said plurality of contact lenses consisting of one contact lens selected based upon empirical data obtained from said single eye, and at least one contact lens selected based upon data of third-party optimal fits;
alpha numeric indicators operable to indicate the chronology to successively place said plurality of contact lenses on said single eye.

2. The system of claim 1, wherein said plurality of contact lenses comprises 2 to 6 contact lenses.

3. The system of claim 1, wherein said plurality of contact lenses differ in a plurality of parameters.

4. The system of claim 1, said parameter comprising one of a spherical correction and cylindrical correction.

* * * * *